(12) United States Patent
Wang et al.

(10) Patent No.: US 8,628,920 B2
(45) Date of Patent: Jan. 14, 2014

(54) METHOD FOR EARLY DIAGNOSIS OF LIVER CANCER AND PREDICTION OF METASTASIS

(75) Inventors: Horng-Dar Wang, Hsinchu (TW); Chiou-Hwa Yuh, Hsinchu (TW); Yung-Chun Hsiao, Hsinchu (TW); Yu-Ting Chou, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 15 days.

(21) Appl. No.: 13/220,055

(22) Filed: Aug. 29, 2011

(65) Prior Publication Data

US 2013/0029317 A1    Jan. 31, 2013

(30) Foreign Application Priority Data

Jul. 27, 2011 (TW) .............................. 100126558 A

(51) Int. Cl.
*C12Q 1/68* (2006.01)

(52) U.S. Cl.
USPC .......................................................... 435/6.1

(58) Field of Classification Search
None
See application file for complete search history.

(56) References Cited

U.S. PATENT DOCUMENTS

2012/0040848 A2*   2/2012   Buendia et al. ................... 506/9

OTHER PUBLICATIONS

Tockman et al (Cancer Res., 1992, 52:2711s-2718s).*

* cited by examiner

*Primary Examiner* — Sean Aeder
(74) *Attorney, Agent, or Firm* — WPAT, P.C.; Anthony King

(57) ABSTRACT

Disclosed is a method for early diagnosis of liver cancer. The method comprises the steps of: (A) providing a sample obtained from a subject; (B) assessing the expression level of four subtypes of α-mannosidase genes consisting of MAN1C1 in the sample; (C) comparing the expression level of α-mannosidase genes in the sample with a normal control; and (D) determining whether the subject having a risk of suffering liver cancer in accordance with the result of step (C); wherein while the MAN1C1 expression level of the sample is lower than that in the normal control, the subject is determined to have a risk of suffering liver cancer. Additionally, while MAN1A1, MAN1A2 and MAN1B1 expression levels in the sample are higher than those in control group, the subject is determined to suffer from liver cancer and has a risk of metastasis.

8 Claims, 15 Drawing Sheets

Figures:

METHOD FOR EARLY DIAGNOSIS OF LIVER CANCER AND PREDICTION OF METASTASIS

CROSS-REFERENCE TO RELATED APPLICATIONS

This Non-provisional application claims priority under 35 U.S.C. §119(a) on Patent Application No(s). [100126558] filed in Taiwan, Republic of China [Jul. 27, 2011], the entire contents of which are hereby incorporated by reference.

FIELD OF THE INVENTION

The present invention relates to a method for diagnosis of liver cancer and metastasis, particularly relates to a method using MAN1C1 for early diagnosis of liver cancer, inhibition of metastasis, and screening drugs for treating liver cancer.

BACKGROUND OF THE INVENTION

Liver cancer is one of the most common malignant tumors in Taiwan, more than 7,000 people died as a result of liver cancer each year. The symptom was not obvious in early stage; the patients feel nothing after having liver cancer for long time. Until the progression of the disease to some degree, it will gradually produce some symptoms such as liver pain, loss of appetite, fatigue, weakness, losing weight etc. At the later stage, patients develop jaundice, ascites, vomiting, coma and other symptoms. Patients with liver cancer often palpable huge tumor on abdominal, however this has come in late, and even metastasis to the lungs and other organs. The overall duration of liver cancer is about two and half years, of which first two years are the early stage without symptoms. Once the symptoms appear, the survival time is only six months. Liver cancer is very difficult to diagnosis. For most of the patients, liver transplantation is their only hope. The method for early diagnosis could save countless lives. Some of the current method of detection of tumor growth is often based on the existence of the blood concentrations of specific markers. For the detection of liver cancer, commonly use α-fetoprotein (AFP) in diagnosing liver cancer. AFP is a normal fetal serum protein synthesized by the liver, yolk sac, and gastrointestinal tract that shares sequence homology with albumin. It is a major component of fetal plasma, reaching a peak concentration of 3 mg/ml at 12 weeks of gestation. AFP can be found in 95% primary liver cancer patients' blood, it is also used as a marker for screening liver cirrhosis and hepatitis. Due to AFP's low specificity, fake positive results are frequently occurs. It is estimated that 6 billion NTD commercial potential exist in Taiwan's market regarding liver caner early diagnosis, and a more gigantic potential exists in foreign market.

The process of N-glycosylation consists of a covalent linkage of a specific oligosaccharide (Glc3Man9GlcNAc2) on a nascent protein. Once the oligosaccharide is transferred, several subsequent steps of maturation will occur along the secretory pathway. N-glycosylation is ubiquitous in eukaryotes. First steps of N-glycosylation are conserved through eukaryotes from yeast to human, which take place in the endoplasmic reticulum. The following and last steps of maturation leading to polymannosylated glycoprotein, which occur in the Golgi apparatus, and are species specific. The function of α-mannosidase is to trim the mammose of the glycoprotein in the process of N-glycosylation. There are many types of α-mannosidase in human. Previous studies revealed that some specific types of mannosidase are related to the formation of cancer, supported with high expression level of mannosidase in particular cancer. Swainsonine (SW), α-mannosidase II inhibitor can efficiently decrease the tumor size in nude mice injected with leukemia cell (MDAY-D2) (Goss, 1995). Deoxymannojirimyci (DMJ), α-mannosidase I inhibitor decreased migration ability of bladder cancer cells (T24) (Przybylo, 2005). DMJ also can induce liver cancer cell (7721) toward apoptosis (Przybylo, 2005). Based on these literatures, the present invention further discover the expression level of four α-mannosidase genes in different stages of liver cancer and their correlation to migration ability. Furthermore, early diagnosis of cancer using α-mannosidase has not been reported previously, and we identified one type of α-mannosidase-MAN1C1 can predict the early stage.

SUMMARY OF THE INVENTION

Though high expression level of α-mannosidase has been known to be associated with specific cancers, and suppressing the activity of α-mannosidase may inhibit growth, induce apoptosis even decrease migration ability of cancer cells. However, early diagnosis of liver cancer using MAN1C1 has not been reported before. Furthermore, expression levels of four α-mannosidase subtypes have never been identified in different liver cancer stages.

One object of the present invention is to provide a method for early diagnosis of liver cancer by low expression of MAN1C1.

Another object of the present invention is to provide a method for determining liver cancer and metastasis by high expression of MAN1A1, MAN1A2 and MAN1B1.

Yet another object of the present invention is to provide a method for inhibiting metastasis by overexpressing MAN1C1 in liver cancer cells.

Yet another object of the present invention is to provide a marker for screening target drug for treating liver cancer.

In one embodiment, the method for early diagnosis of liver cancer comprises the steps of: (A) providing a sample obtained from a subject; (B) assessing the expression level of four subtypes of α-mannosidase genes consisting of MAN1A1, MAN1A2, MAN1B1 and MAN1C1 in the sample; (C) comparing the expression level of α-mannosidase genes in the sample with a normal control; and (D) determining whether the subject having a risk of suffering liver cancer in accordance with the result of step (C); wherein while the MAN1C1 expression level of the sample is lower than that in the normal control, the subject is determined to have a risk of suffering liver cancer. Additionally, while MAN1A1, MAN1A2 and MAN1B1 expression levels in the sample are higher than those in control group, the subject is determined to suffer from liver cancer and has a risk of metastasis.

Preferably, the expression levels of MAN1A1, MAN1A2, MAN1B1 and MAN1C1 in the sample are at least two folds higher or lower than those in the normal control; wherein step (D) further comprises comparing MMP9 expression level in the sample with a normal control, while MAN1A1, MAN1A2 and MAN1B1 expression levels in the sample are higher than those in control group, and the MMP9 expression level in the sample is higher than in the normal control, the subject is determined to have a risk of liver metastasis. The expression level of α-mannosidase (MAN1A1, MAN1A2, MAN1B1 and MAN1C1) and MMP9 mentioned above can be either RNA or protein, and the subject is hepatitis B virus carrier, and the sample is a liver tissue obtained from the subject.

In another embodiment, the method of inhibiting metastasis in liver cancer cell comprises a step of overexpressing MAN1C1 in a liver cancer cell so as to inhibit liver metastasis.

Preferably, overexpressing MAN1C1 can inhibit the MMP9 expression level in the liver cancer cell.

In yet another embodiment, the method of screening a drug for liver cancer, comprises the steps of: (A) providing a liver cancer cell treated with a drug; (B) assessing MAN1C1 expression level of the liver cancer cell; (C) determining whether the drug has a therapeutical effect according to the MAN1C1 expression level.

In the future, MAN1C1 can be applied to early diagnosis of liver cancer and metastasis, suppression of liver metastasis, and screening agents for treating liver cancer.

The embodiments of the present invention are further described through below detailed examples and the drawings.

DETAILED DESCRIPTION

A method for early diagnosis of liver cancer and prediction of metastasis is described with reference to the preferred embodiments below, it is apparent to those skilled in the art that a variety of modifications and changes may be made without departing from the scope of the present invention which is intended to be defined by the appended claims.

Figure 1:
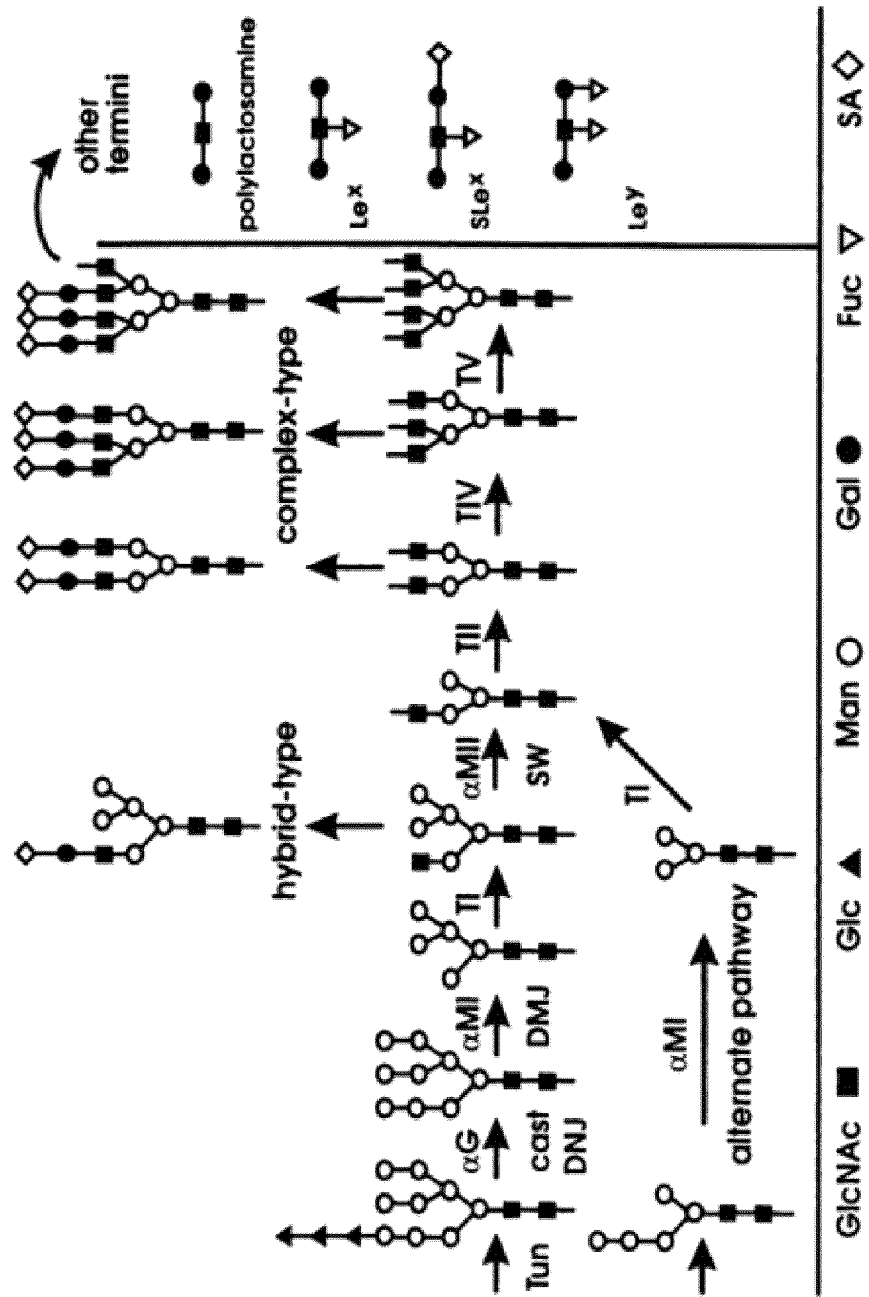
FIG. 1 demonstrates the Golgi N-linked carbohydrate processing pathway.

FIG. 1 demonstrates the Golgi N-linked carbohydrate processing pathway. As shown in FIG. 1, α-1,2 mannosidase I plays a role for trimming carbohydrate branches in carbohydrate processing. The inhibitors such as DMJ and SW can inhibit oligosaccharide chain trimming. Oligosaccharide chain synthesis and processing includes a series of glycoside hydrolases, such as glucosidase (i.e. glucosidase II) and mannosidase (i.e. mannosidase I and mannosidase II). Mannosidase I and mannosidase II mainly present in Golgi apparatus, these enzymes can be inhibited and terminate the Golgi N-linked carbohydrate processing, so as to produce high-mannose and complex-type N-linked glycans. α-1,2 mannosidase I inhibitor DMJ and α-mannosidase II inhibitor SW can influence glycan epitope expression and further inhibit tumor cell migration, invasion and growth in vitro, which shows a potential ability of inhibiting cancer metastasis.

Figure 2:
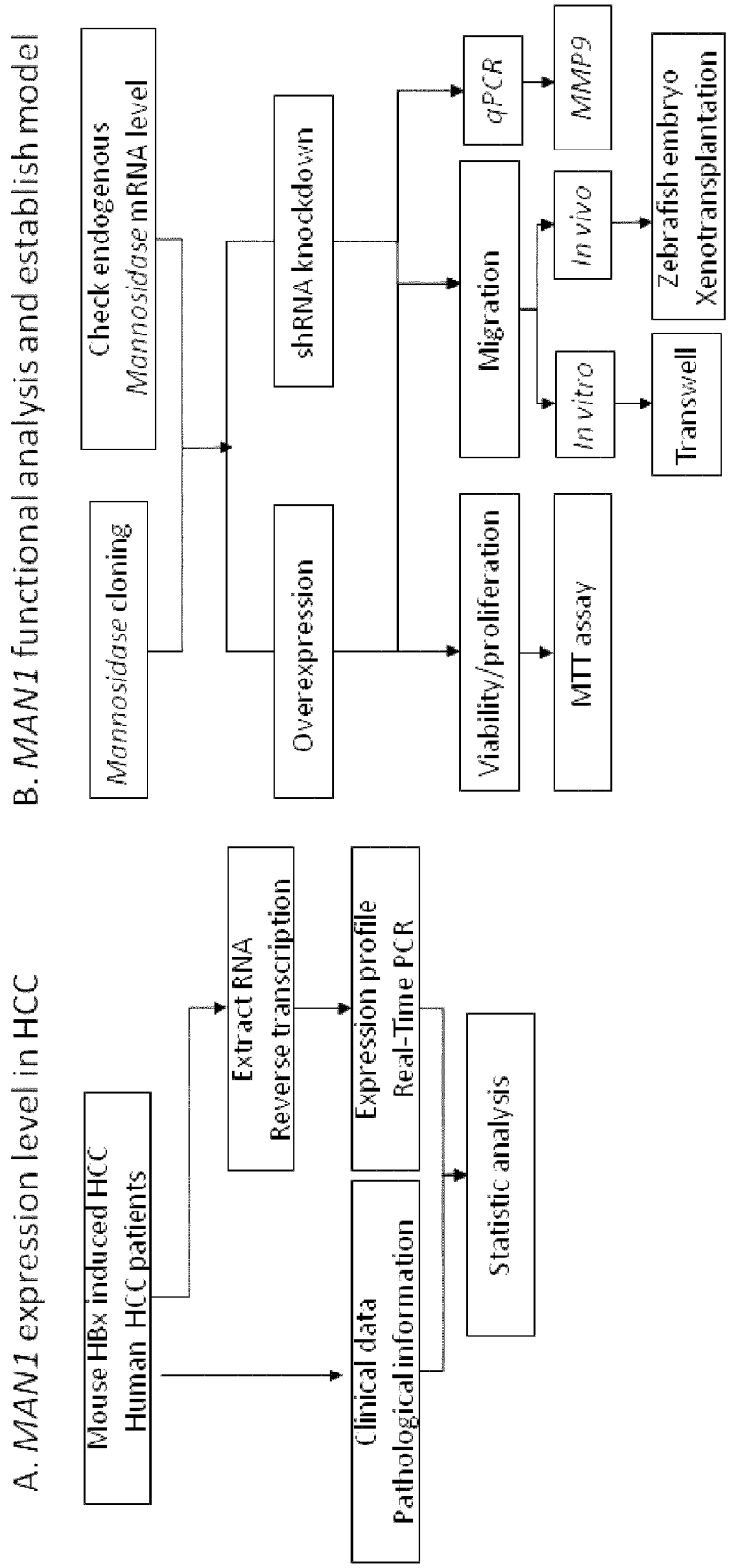
FIG. 2A-2B demonstrate a flowchart of experiments in the present invention.
Figure 3A:
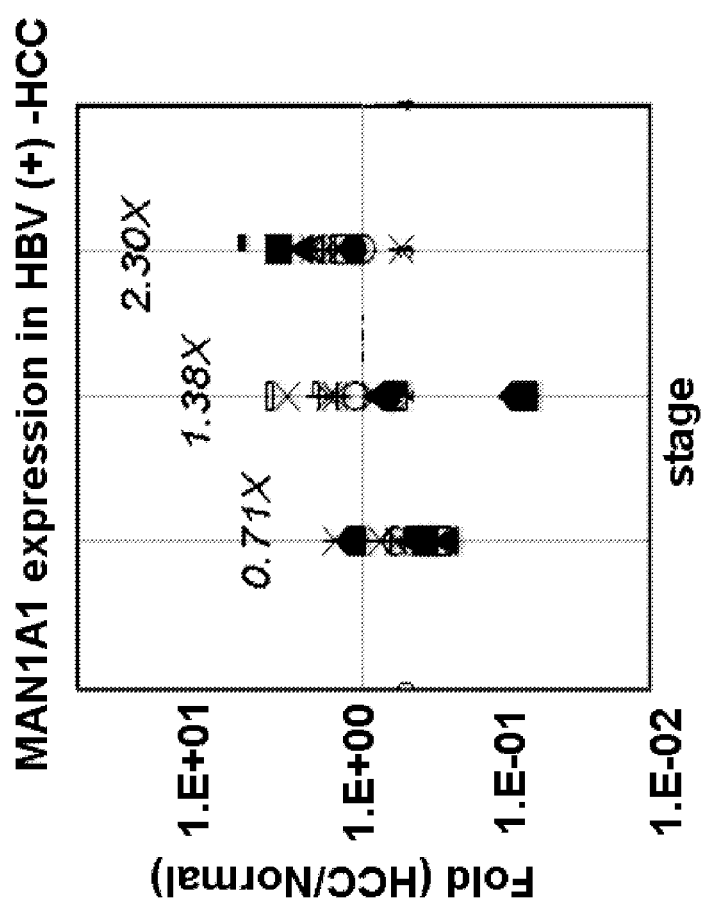
FIG. 3 demonstrates MAN1A1, MAN1A2, MAN1B1, MAN1C and MAN1C1 expression levels using the samples of human liver cancer patients carry hepatitis B virus.
Figure 3B:
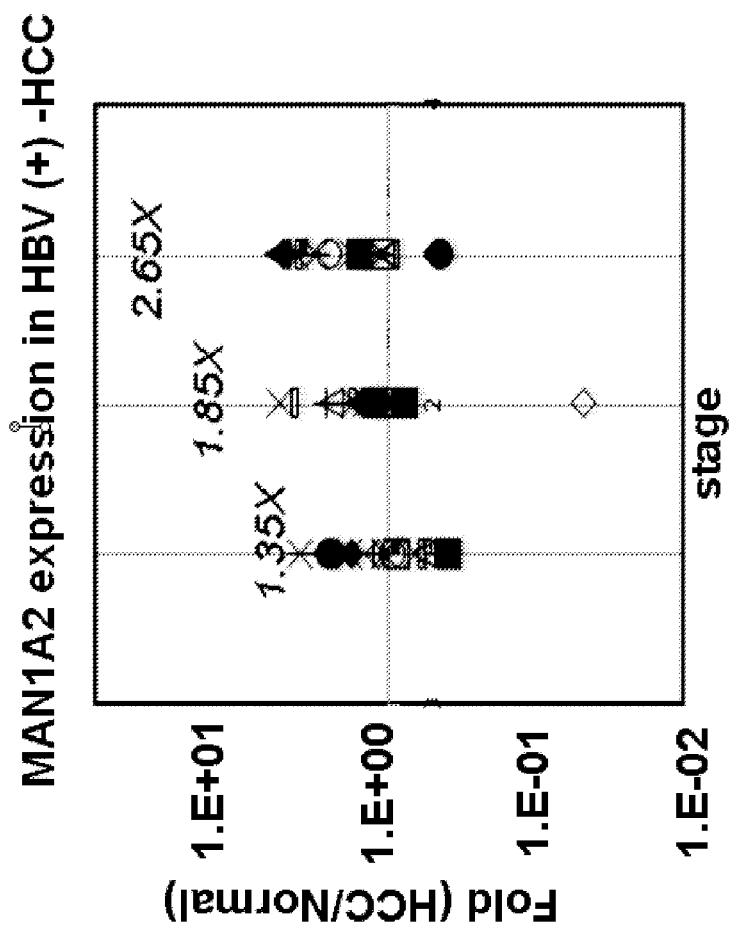
Figure 3C:
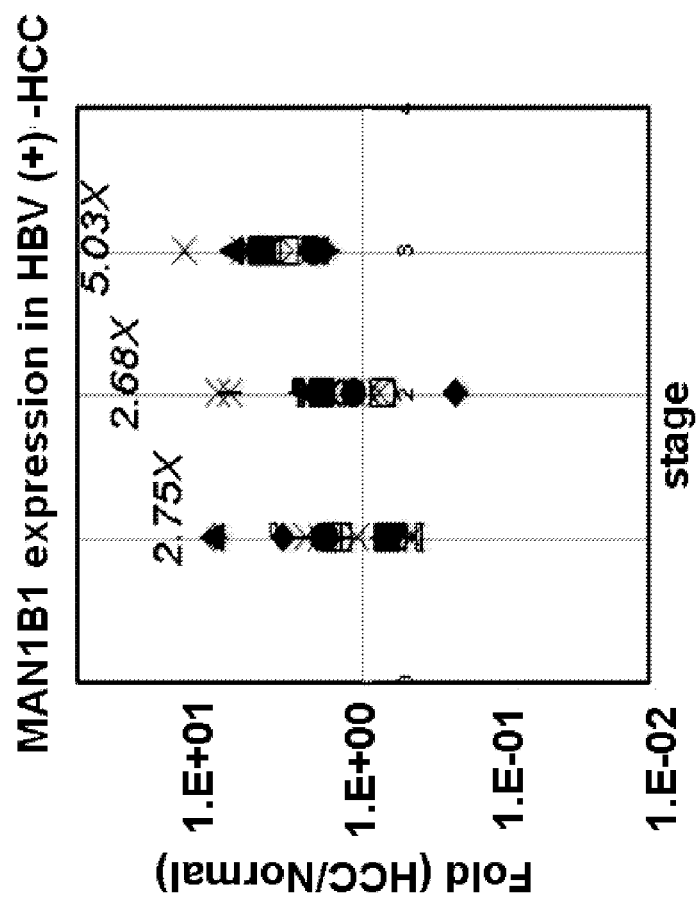
Figure 3D:
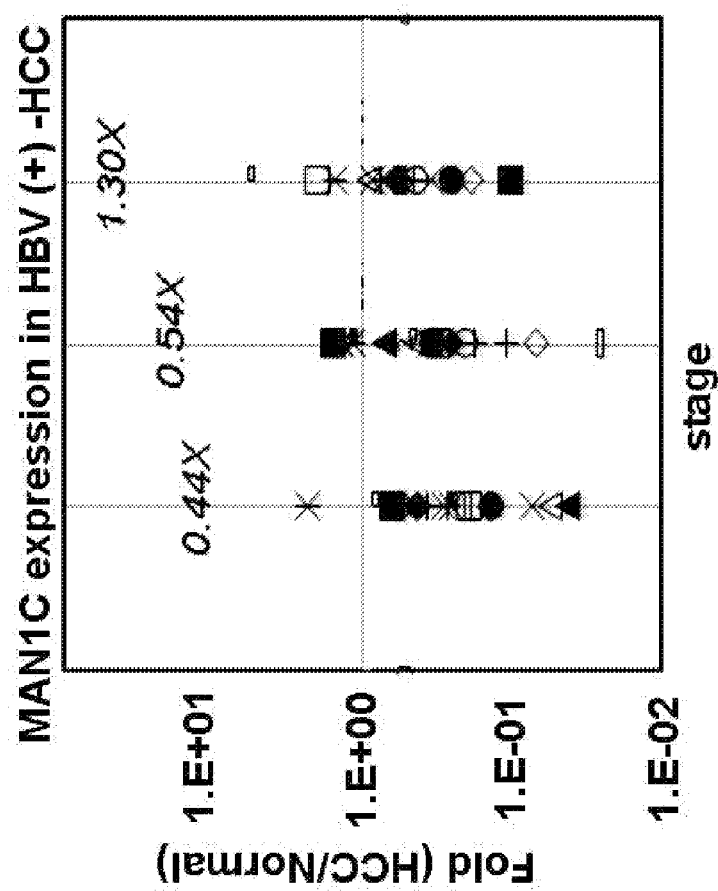
Figure 3E:
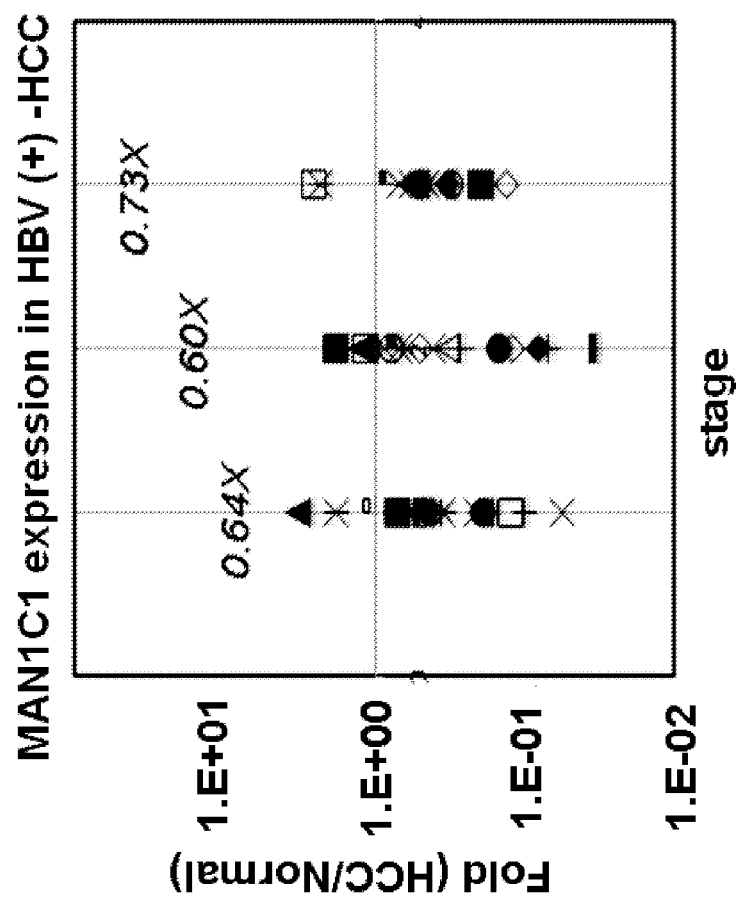

FIG. 2A-2B demonstrate a flowchart of experiments in the present invention. As shown in FIG. 2A, the quantitative PCR was performed to assess endogenous α-1,2 mannosidase mRNA in mice and human. As shown in FIG. 2B, MAN1A1, MAN1A2, MAN1B1 and MAN1C1 cloning was performed. Overexpression and shRNA knockdown of α-1,2 mannosidase were performed in the in vitro cell migration assay. Also a MAN1C1 stable transfected cell line was established and injected into zebrafish embryo, and an in vivo cell migration assay was then performed. Simultaneously, Q-PCR experiment was performed to assess if MMP9 mRNA level has changed due to α-1,2 mannosidase overexpression.

FIG. 3 demonstrates MAN1A1, MAN1A2, MAN1B1, MAN1C and MAN1C1 expression levels in liver tissue obtained from hepatitis B virus positive liver cancer patients. As shown in FIG. 3A-3E, MANA1, MANA2, MANB1, MAN1C and MAN1C1 mRNA level of liver cancer patients were assessed by Q-PCR, wherein MAN1C was part of MAN1C1. Those patients were separated into three stages: stages I, II and III, the latter stage represents the more aggressive cancerous condition. The cancerous liver tissue was used as experiment group, and the non-cancerous liver tissue obtained from the same patient was used as a control group. In cancerous tissue, two-fold expression higher than control group was defined as overexpression, and two-fold expression lower than control group was defined as decreased expression. As shown in FIG. 3A-3E, MAN1A1, MAN1A2 and MAN1B1 were elevated aggressive cancerous condition, particularly two folds than normal liver tissue. However, MAN1C1 expression in the early stage liver cancer patient was lower than that in normal liver tissue with 2 folds.

Figure 4:
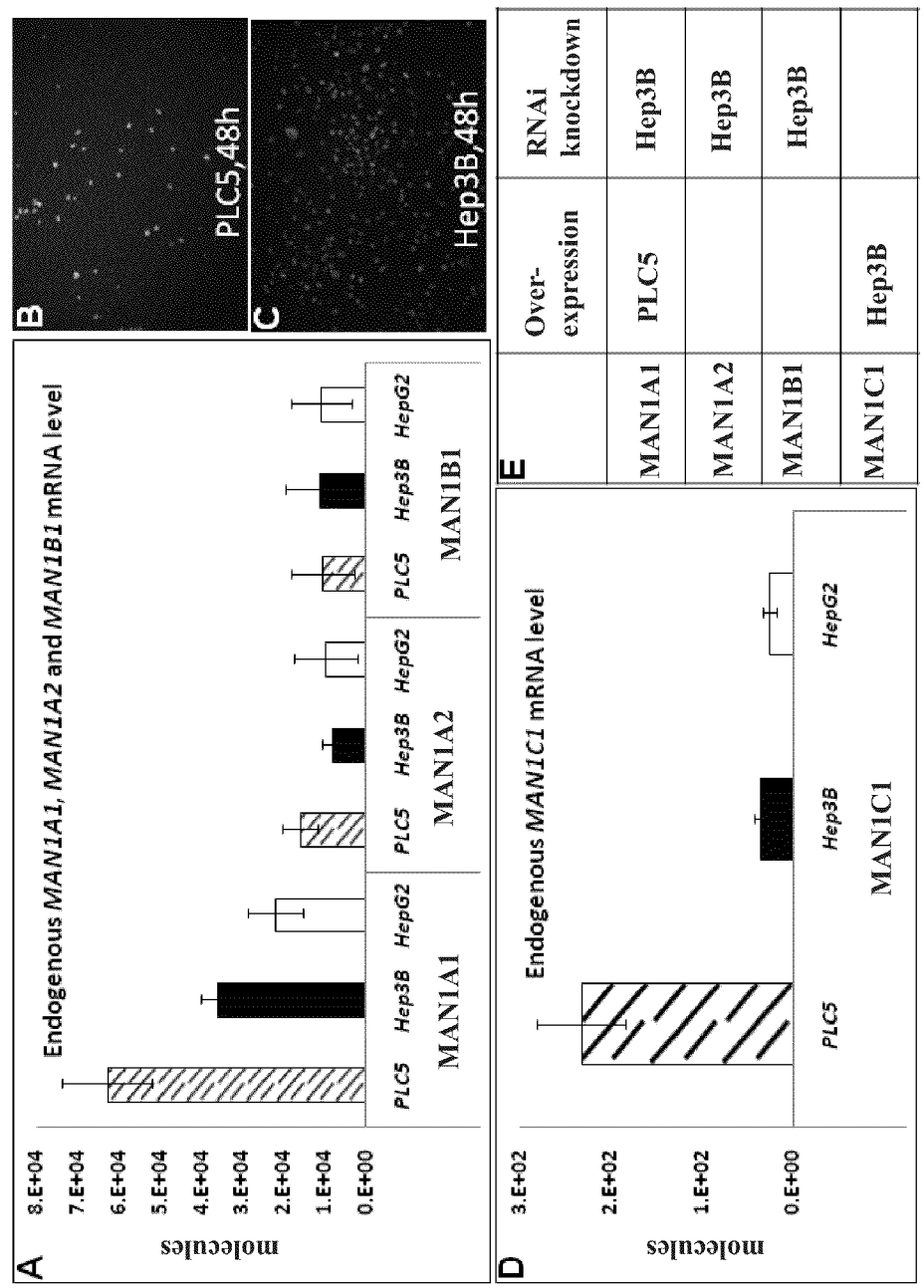
FIG. 4 demonstrates the Q-PCR result of endogenous MAN1A1, MAN1A2, MAN1B1, and MAN1C1 expression levels in different cell lines.

FIG. 4 demonstrates the Q-PCR result including: (A) endogenous MAN1A1, MAN1A2 and MAN1B1 RNA levels; performing in vitro cell migration assay in different cell lines (B) PLC5 and (C) Hep3B, to determined which cell line for further overexpression and knockdown experiments (D) endogenous MAN1C1 RNA levels in different cell lines. A serial dilution ($10^{-3}$~$10^{-9}$) was performed by using green fluorescent protein (GFP) DNA with known molecule numbers to be a standard curve. By using the standard curve, Ct value was calculated to molecule numbers by interpolation, such that endogenous MAN1A1, MAN1A2, MAN1B1 and MAN1C1 mRNA numbers in PLC5, Hep3B and HepG2 cells were obtained. $10^5$ cells were added in 300 μl of serum free DMEM and incubated on a transwell culture dish which had a membrane with 6.4 mm diameter and 8.0 μl pore size. 500 μl medium (10% FBS in DMEM) was added into lower chamber, and the dish was incubated at 37° C. for 48 hours, and the cells in the lower chamber was stained with 1×DAPI and calculated. The result was shown in figure, endogenous α-1,2 mannosidase mRNA levels were varied in different cells, and the migration ability of Hep3B was greater than PLC5. According to endogenous mRNA level and cell migration ability (E), PLC5 cell line was determined to be used in MAN1A1 overexpression experiment, Hep3B was determined to be used in MAN1A1, MAN1A2 and MAN1B1 knockdown experiments, and MAN1C1 overexpression was performed in Hep3B.

Figure 5:
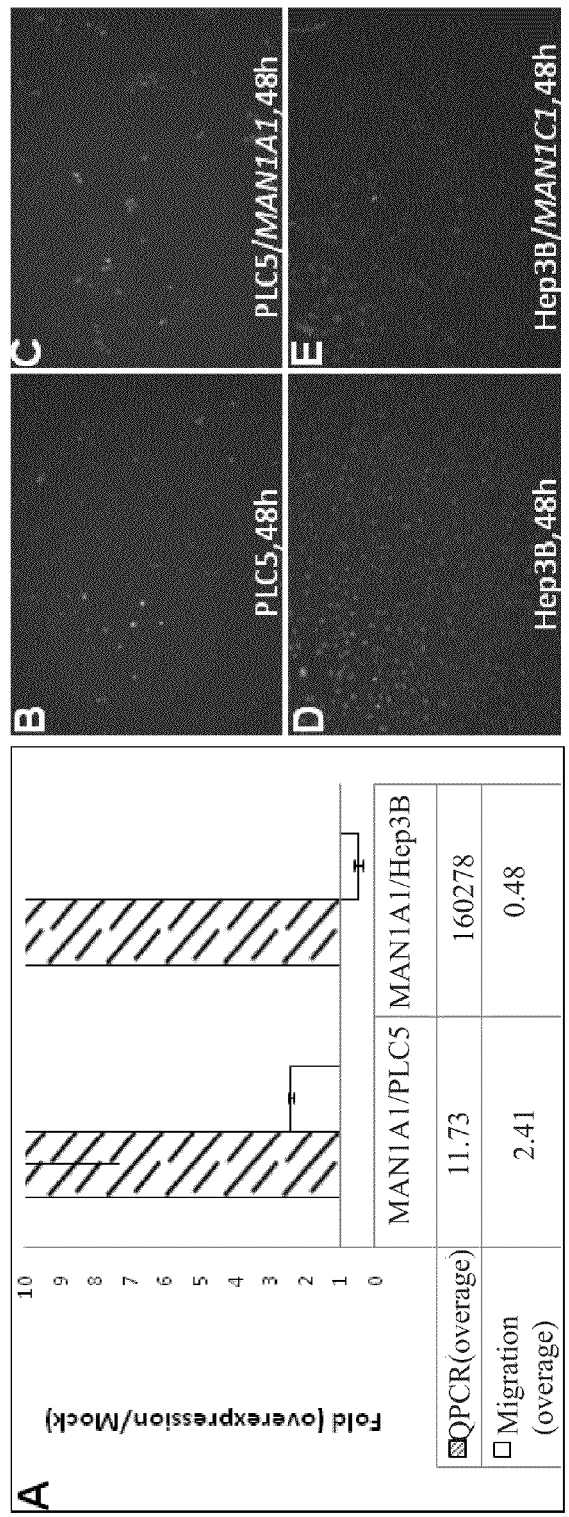
FIG. 5A-5E demonstrate the cell migration assay results after overexpression of MAN1A1 and MAN1C1.
Figure 6:
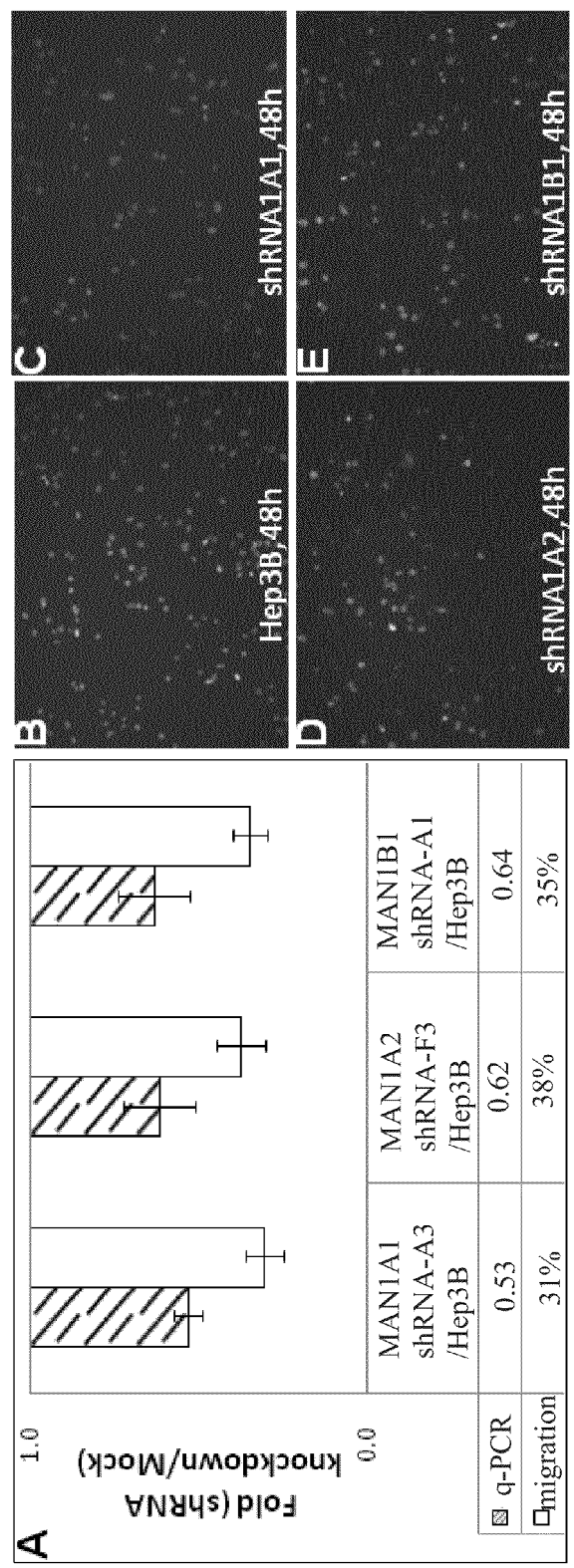
FIG. 6A-6E demonstrate the cell migration assay results after shRNA knockdown of MAN1A1, MAN1A2 and MAN1B1.

FIG. 5A-5E demonstrate the cell migration assay results after overexpression of MAN1A1 and MAN1C1 for two days. As shown in FIG. 5A, Q-PCR was performed to quantify MAN1A1 and MAN1C1 mRNA expression level, and untransfected cells (mock) were used as control. Cell migration assay results were shown in FIGS. 5B, 5C, 5D and 5E, and the method used was similar to FIGS. 4B and 4C. Results shown in FIG. 5A demonstrated that MAN1A1 and MAN1C1 mRNA were successfully elevated to 11.73 and 160278 folds as compared with Hep3B. Furthermore, MAN1A1 overexpression advanced the ability of cell migration to 2.41 folds, and MAN1C1 overexpression reduced the ability of cell migration to 0.48 folds. FIGS. 5B and 5C are photos which demonstrate cell migration assay results of PLC5 and MAN1A1 overexpression in PLC5. FIGS. 5D and 5E are photos which demonstrate cell migration assay results of Hep3B and MAN1C1 overexpression in Hep3B.

FIG. 6A-6E demonstrate the cell migration assay results after shRNA knockdown of MAN1A1, MAN1A2 and MAN1B1 for two days. As shown in FIG. 5A, Q-PCR was performed to quantify MAN1A1, MAN1A2 and MAN1B1 mRNA expression level, and untransfected cells (mock) were used as control. Cell migration assay results were shown in FIGS. 6B, 6C, 6D and 6E, and the method used was similar to FIGS. 4B and 4C. Results shown in FIG. 6A demonstrated that MAN1A1, MAN1A2 and MAN1B1 mRNA after knockdown with shRNA were successfully reduced to 55%, 62% and 64% as compared with untransfected Hep3B cells. Furthermore, MAN1A1, MAN1A2 and MAN1B1 knockdown reduced the ability of cell migration to 31%, 38% and 45% as compared with untransfected Hep3B cells. FIG. 6B-6E are photos which demonstrate cell migration assay results of Hep3B before (B) and after shRNA knockdown of MAN1A1 (C), MAN1A2 (D) and MAN1B1(E).

Figure 7:
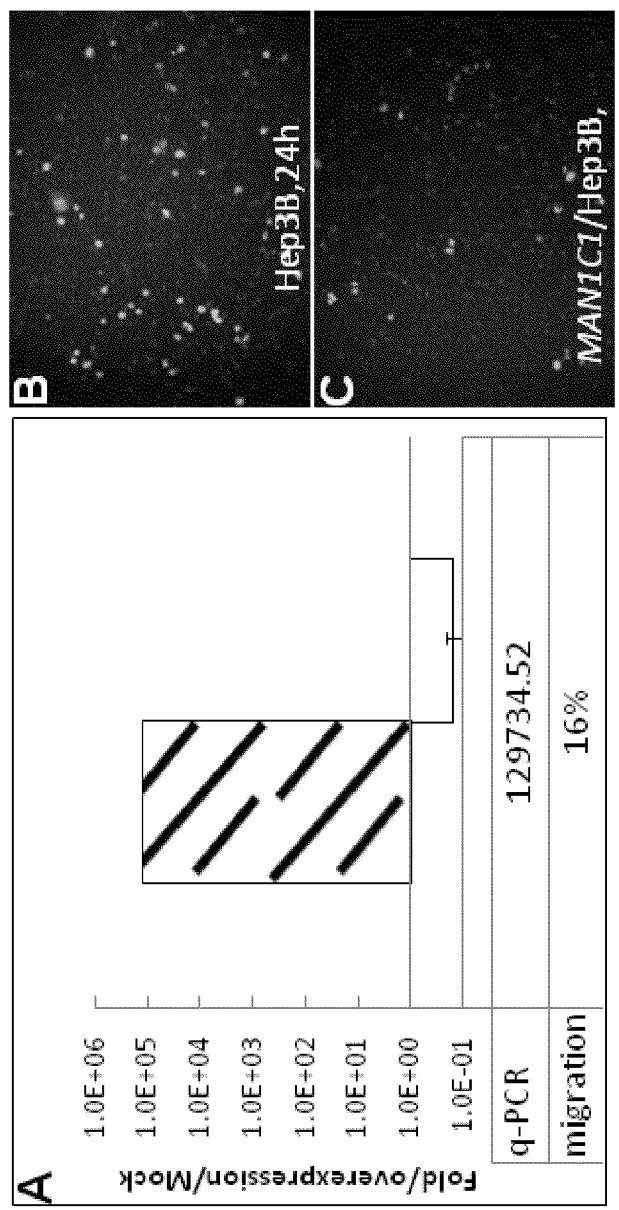
FIG. 7A-7C demonstrate the cell migration assay results after stable overexpression of MAN1C1 in Hep3B (MAN1C1/Hep3B).

FIG. 7A-7C demonstrate the cell migration assay results after stable overexpression of MAN1C1 in Hep3B (MAN1C1/Hep3B). Stable overexpressed Hep3B was used as experiment group, and original Hep3B was used as control group. Methods used in FIG. 7A: Q-PCR was performed to quantify MAN1C1 mRNA expression level, and untransfected cells (mock) were used as control. The cell migration assay performed in FIGS. 7B and 7C were similar to FIGS. 4B and 4C, except the analyzing time was after 24 hr. As shown in figures, cell migration ability of cells with stable overexpression of MAN1C1 was reduced to 16% as compared with original Hep3B. FIGS. 7B and 7C are photos which demonstrate cell migration assay results of Hep3B and stable overexpression of MAN1C1 in Hep3B.

Figure 8:
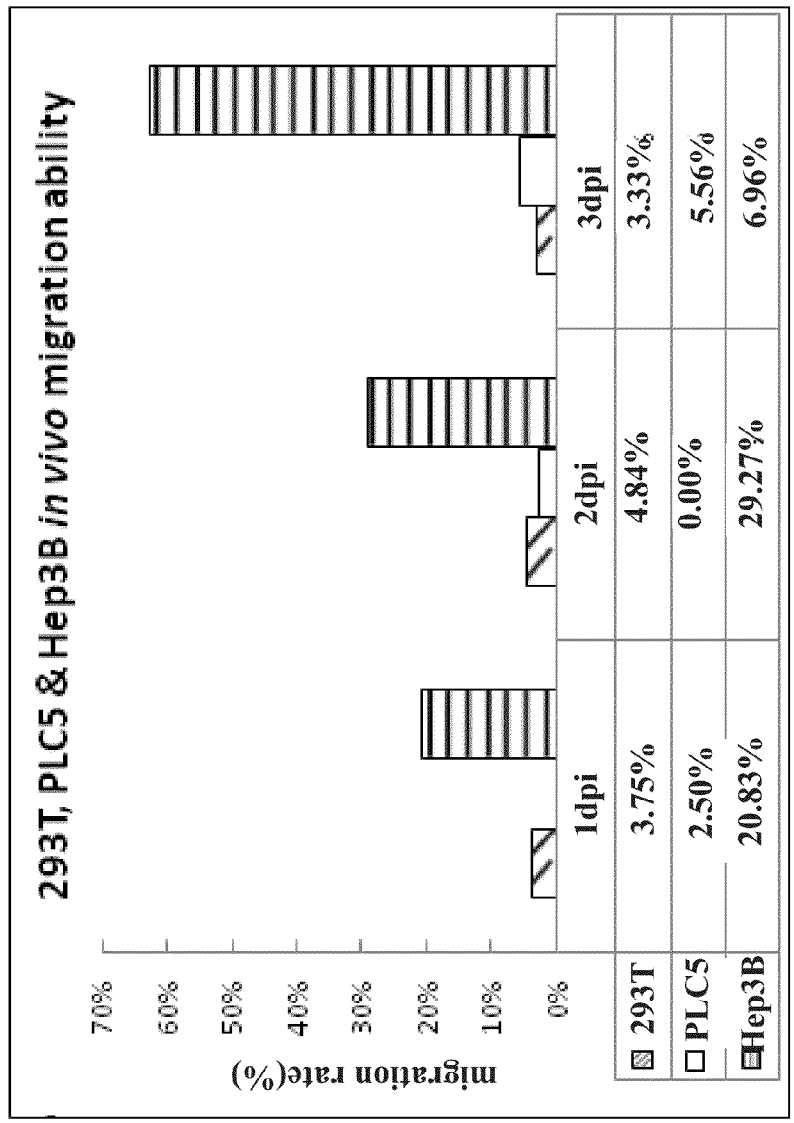
FIG. 8 demonstrate the in vivo cell migration assay results of 293T, PLC5 and Hep3B cells by xenotransplantation into zebrafish.

FIG. 8 demonstrate in vivo cell migration assay results of 293T, PLC5 and Hep3B cells by xenotransplantation to zebrafish embryos. 293T is a transformed human kidney cell line. PLC5 and Hep3B are human hepatoma cell lines. Establishment of the xenotransplantation zebrafish animal model in FIG. 8: using DiI to label the suspension of cells and incubated in PBS before injection, and the labeled cells were microinjected into 2 days old zebrafish embryos. Each injection amount was 4.6 nl and contained 400 cells, and the injection position was the rear of yolk. The injected cells were monitored for 3 days after injection. Previous in vitro experiment results found that migration ability of Hep3B was greater than PLC5, and the identical conclusion was once identified by in vivo experiment, and the 293T were noncancerous control. According to statistic analysis results, cell migration was observed in 3.33% of zebrafish after injection of 293T cells. Three days after injection, cell migration was observed in 62% of zebrafish after injection of Hep3B cells. These results were consistent with the previous in vitro experiments. After 3 days of microinjection, 293T and PLC5 cells were still retained in yolk cavity. The position of yolk cavity where Hep3B cells injected. The cells were found to migrate to tail after 1 day of injection.

Figure 9:
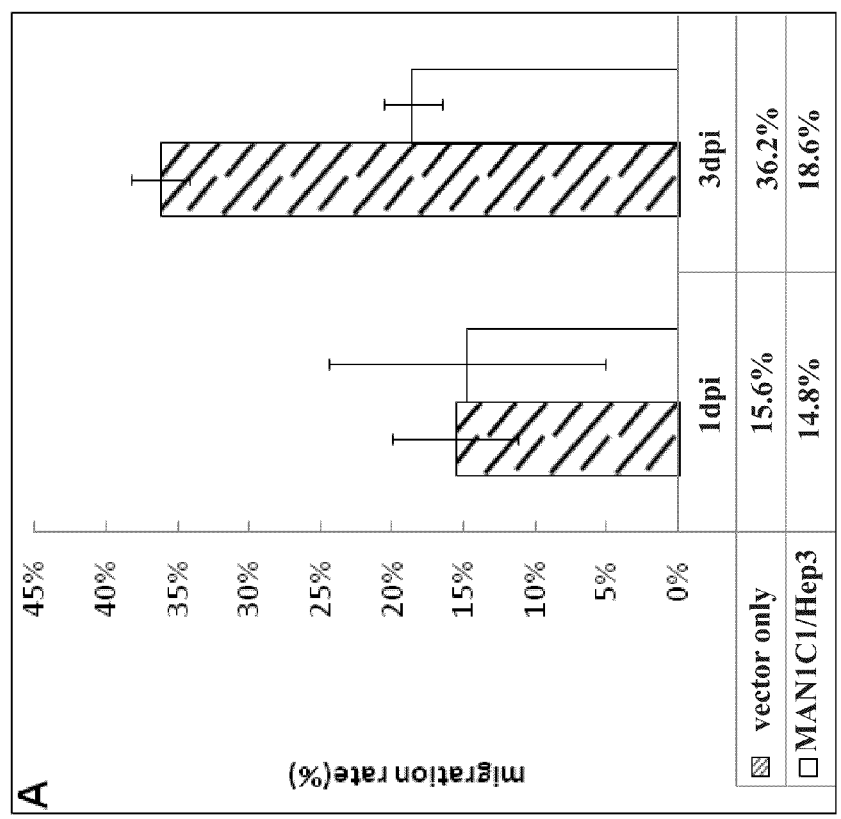
FIG. 9 demonstrate the cell migration assay results of MAN1C1-overexpressed Hep3B cells (MAN1C1/Hep3B) by in vivo xenotransplantation into zebrafish.

FIG. 9 demonstrate the cell migration assay results of MAN1C1-overexpressed Hep3B cells (MAN1C1/Hep3B) by in vivo xenotransplantation. Stable overexpression of MAN1C1 in Hep3B was used as experiment group, and Hep3B was used as control. The cells of experiment group and control were microinjected into zebrafish yolk. Each injection contains 400 labeled cells, and these cells were observed and recorded at $1^{st}$ and $3^{rd}$ day. The method used was similar to FIG. 8, however experiment group was stable overexpressed MAN1C1 Hep3B, and the control contained large amount of expression vectors. According to statistic analysis results, cell migration ability was 18.6% in experiment group, and cell migration ability was 36.2% in control group. According to the results, three days after injection, cell migration ability of stable overexpressed MAN1C1 in Hep3B was two folds than original Hep3B. The cells were found to migrate to tail in control group after 1 day of injection, this result was also found after 3 days of injection. 80% of MAN1C1/Hep3B cells were observed that Hep3B cells were retained in yolk cavity after 3 days of injection.

Figure 10:
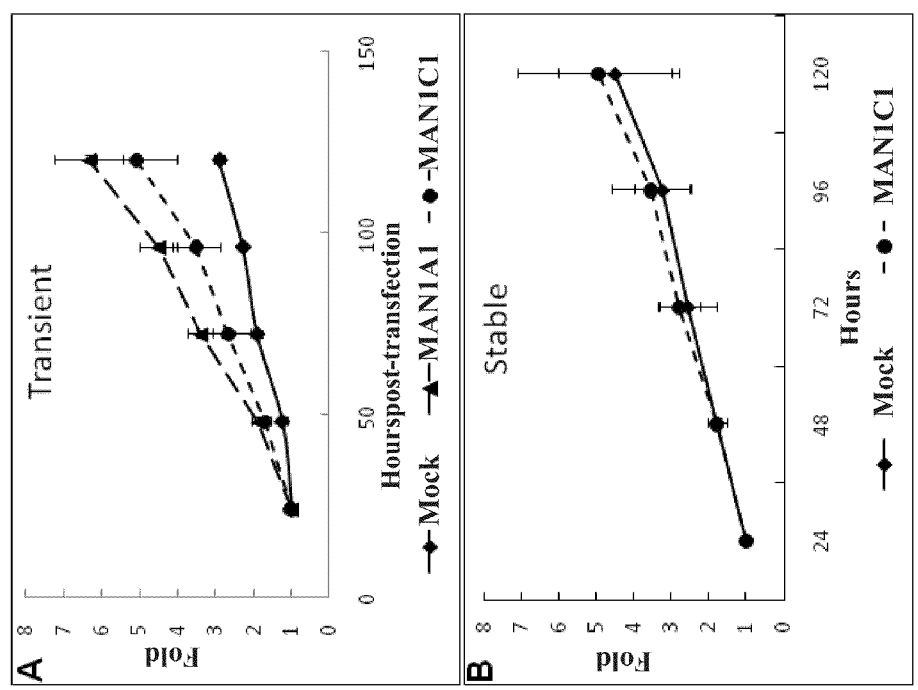
FIG. 10 demonstrate the MTT assay result.

FIG. 10 demonstrates MTT assay result. X-axis represents time (hour), and Y-axis represents proliferation fold. Experiment method: 1. 6,000 cells were seeded on a 96-well culture dish. 2. 200 µl of mixed medium (MTT:DMEM=1:9) was added into the dish every 24 hr, and cells were incubated for 3 hr at 37° C. 3. 100 µl of DMSO was used to break the cells, and absorbance value ($OD_{570nm}$) of each sample was measured. Experiment group: overexpression of MAN1A1 in Hep3B (A) or stable overexpression of MAN1C1 in Hep3B (B). Control group: nontransfected Hep3B cells. As shown in MTT assay results of FIG. 10A, overexpression of MAN1A1 promotes Hep3B cells growing faster than nontransfected cells. As shown in FIG. 10B, the growth curves of experiment group (overexpression of MAN1C1) and control has no difference.

Figure 11:
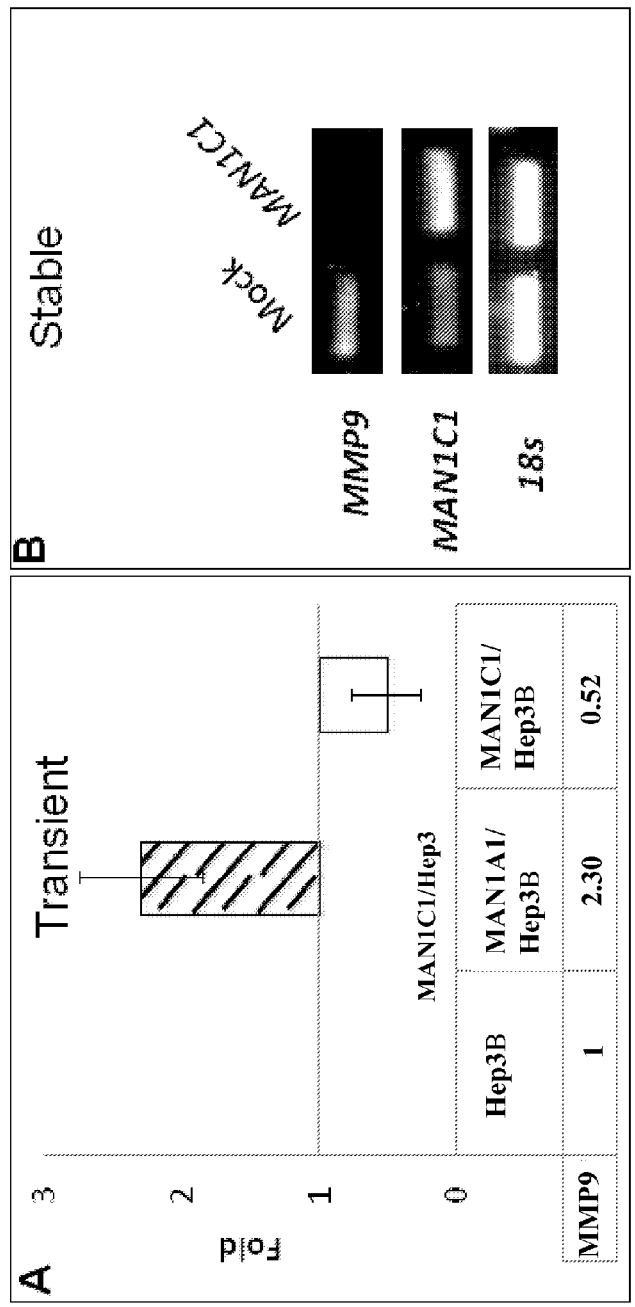
FIG. 11A-11B demonstrate MMP9 expression level in MAN1C1-overexpressed cells.

FIG. 11A-11B demonstrate MMP9 expression level in MAN1A1 or MAN1C1-overexpressed cells. As shown in FIG. 11A, Q-PCR was used to assess MMP9 expression level, untransfected cells were used as control and expression more than 2 folds was defined as overexpression. The results suggest overexpression of MAN1A1 increased MMP9 expression to 2.3 folds than control, and overexpression of MAN1C1 suppressed MMP9 expression to 0.33 folds. As shown in FIG. 11B, RT-PCR was performed to amplify MAN1C1 and MMP9 cDNA, and 18s RNA was used as control. MMP9 expression in stable overexpression MAN1C1 Hep3B cells was reduced in comparison with control group.

As results disclosed in the present invention, three genes: MAN1A1, MAN1A2 and MAN1B1 were overexpressed in liver cancer when compare to the normal counterpart. However, the expression of MAN1C1 was down-regulated in HCC patients when compare to normal liver tissues. Moreover, 94% of HBV carrier HCC patients exhibit over two-fold decreased MAN1C1 expression as early as stage I. This result indicated that the decreasing expression of MAN1C1 might be a potential biomarker for early diagnosis for HCC. Those expression patterns implied MAN1A1, MAN1A2 and MAN1B1 probably are potential oncogenes, and the MAN1C1 might functions as tumor suppressor. In order to study the role of four α-mannosidase genes during hepatocarcinogenesis, we first cloned the genes for MAN1A1, MAN1A2, MAN1B1 and MAN1C1, and used cell line to investigate the proliferation, migration and other genes' expression after over-expressed or knockdown those genes. It was found that overexpression of MAN1A1 into PLC5 cells can enhance the migration ability, and knockdown of MAN1A1, MAN1A2 and MAN1B1 can decrease the migration ability in Hep3B cells. On the other hand, overexpression MAN1C1 in Hep3B cell decreased migration ability by in vitro transwell assay. To further determine how α-1,2 mannosidase I influenced migration ability, hepatic cell lines with stable overexpression of α-1,2 mannosidase I were thus established. Zebrafish embryo was used to perform in vivo xenotransplantation to observe hepatic cancerous cells migration in vivo, and found that migration ability of MAN1C1/Hep3B stable cell line was reduced in zebrafish embryo. To further study the relationship between α-mannosidase genes and cell migration, we focus on matrix metalloproteinases (MMPs) which are proteases to promoted cancer cells growth, migration, invasion and metastasis (Egeblad and Werb, 2002). According to Q-PCR results, it was suggested that overexpression of MAN1A1 increased MMP9 mRNA expression level, and overexpression of MAN1C1 decreased MMP9 mRNA expression level. Due to MMPs are capable of degrading all kinds of extracellular matrix proteins, decreased MMP9 expression means that cell migration and invasion ability is inhibited. According to disclosure of the present invention, it is demonstrated that early reduction of MAN1C1 overexpression in liver cancer patients has potential to be a molecular marker for screening early liver cancer. As proved in cell migration assay, no matter in vivo or in vitro experiment results suggest that MAN1C1 is capable of inhibiting cell migration ability of hepatic cancerous cells.

In conclusion, MAN1C1 has potential to be a tumor suppressor gene and apply to early diagnosis for liver cancer. In one embodiment, the method for early diagnosis of liver cancer comprises the steps of: (A) providing a sample obtained from a subject; (B) assessing the expression level of four subtypes of a-mannosidase genes consisting of MAN1A1, MAN1A2, MAN1B1 and MAN1C1 in the sample; (C) comparing the expression level of α-mannosidase genes in the sample with a normal control; and (D) determining whether the subject having a risk of suffering liver cancer in accordance with the result of step (C); wherein while the MAN1C1 expression level of the sample is lower than that in the normal control, the subject is determined to have a risk of suffering liver cancer. Additionally, while MAN1A1, MAN1A2 and MAN1B1 expression levels in the sample are higher than those in control group, the subject is determined to suffer from liver cancer and has a risk of metastasis.

Preferably, the expression levels of MAN1A1, MAN1A2, MAN1B1 and MAN1C1 in the sample are at least two folds higher or lower than those in the normal control; wherein step (D) further comprises comparing MMP9 expression level in the sample with a normal control, while MAN1A1, MAN1A2 and MAN1B1 expression levels in the sample are higher than those in control group, and the MMP9 expression level in the sample is higher than in the normal control, the subject is determined to have a risk of liver metastasis. The expression level of α-mannosidase (MAN1A1, MAN1A2, MAN1B1 and MAN1C1) and MMP9 mentioned above can be either RNA or protein, and the subject is hepatitis B carrier, and the sample is a liver tissue obtained from the subject.

In another embodiment, the method of inhibiting metastasis in liver cancer cell comprises a step of overexpressing MAN1C1 in a liver cancer cell so as to inhibit liver metastasis. Preferably, overexpressing MAN1C1 can inhibit the MMP9 expression level in the liver cancer cell.

In yet another embodiment, the method of screening a drug for liver cancer, comprises the steps of: (A) providing a liver cancer cell treated with a drug; (B) assessing MAN1C1 expression level of the liver cancer cell; (C) determining whether the drug has a therapeutical effect according to the MAN1C1 expression level.

Although the present invention is described with reference to the preferred embodiments thereof, it is apparent to those skilled in the art that a variety of modifications and changes may be made without departing from the scope of the present invention which is intended to be defined by the appended claims.

What is claimed is:

1. A method for determining risk of metastatic liver cancer, comprising the steps of:
   (A) providing a sample obtained from a subject;
   (B) assessing the RNA expression level of four subtypes of α-mannosidase genes consisting of MAN1A1, MAN1A2, MAN1B1 and MAN1C1 in the sample by detecting MAN1A1, MAN1A2, MAN1B1 and MAN1C1 RNA expression levels in the sample;
   (C) comparing the MAN1A1, MAN1A2, MAN1B1 and MAN1C1 expression levels in the sample with MAN1A1, MAN1A2, MAN1B1 and MAN1C1 expression levels in a normal control; and
   (D) determining whether the subject has a risk of metastasis of liver cancer in accordance with the result of step (C);
   wherein a subject with MAN1A1, MAN1A2 and MAN1B1 expression levels in the sample that are higher than those in the normal control, and MAN1C1 expression level in the sample that is lower than that of the normal control has a high risk of metastasis of liver cancer,
   wherein the sample and the normal control are liver biopsies.

2. The method as claimed in claim 1, wherein MAN1A1, MAN1A2, and MAN1B1 expression levels in the sample are at least two folds higher than those in the normal control.

3. The method as claimed in claim 1, wherein step (D) further comprises comparing MMP9 expression level in the sample with a normal control.

4. The method as claimed in claim 1, wherein while the MMP9 expression level in the sample is higher than the normal control, the subject is determined to have a risk of liver metastasis.

5. The method as claimed in claim 1, wherein the expression level of MAN1A1, MAN1A2, and MAN1B1 can be either RNA or protein.

6. The method as claimed in claim 3, wherein the expression level of MMP9 can be either RNA or protein.

7. The method as claimed in claim 1, further comprising overexpressing MAN1A1, MAN1A2, and MAN1B1 to enhance the MMP9 expression level, and overexpressing MAN1C1 to inhibit the MMP9 expression level.

8. The method as claimed in claim 6, further comprising overexpressing MAN1C1 to inhibit the MMP9 expression level.

* * * * *